United States Patent [19]

Morelle et al.

[11] Patent Number: 4,859,653

[45] Date of Patent: Aug. 22, 1989

[54] USE OF COMPOSITIONS OF MATTER CONTAINING N-ACYLATES OF ALPHA AMINOACIDS FOR THE TREATMENT OF SKIN

[76] Inventors: Jean V. Morelle; Eliane M. T. Lauzanne-Morelle, both of 170 Avenue Parmentier, 75010 Paris, France

[21] Appl. No.: 940,184

[22] Filed: Dec. 9, 1986

Related U.S. Application Data

[63] Continuation of Ser. No. 748,777, Jun. 25, 1985, abandoned, which is a continuation of Ser. No. 567,767, Jan. 3, 1984, abandoned, which is a continuation of Ser. No. 358,848, Mar. 17, 1982, abandoned.

[30] Foreign Application Priority Data

Apr. 2, 1981 [FR] France ............................... 81 06592
Apr. 2, 1981 [FR] France ............................... 81 06593
Apr. 2, 1981 [FR] France ............................... 81 06594

[51] Int. Cl.[4] .................. A61K 37/00; A61K 31/195

[52] U.S. Cl. ......................................... 514/2; 514/423; 514/547; 514/562; 514/563; 514/564; 514/566

[58] Field of Search .................. 514/2, 413, 547, 562, 514/563, 564, 566

[56] References Cited

U.S. PATENT DOCUMENTS 4,208,421  6/1980  Morelle et al. ...................... 424/274

FOREIGN PATENT DOCUMENTS 2152486  4/1973  France .

Primary Examiner—Leonard Schenkman
Attorney, Agent, or Firm—Lucas & Just

[57] ABSTRACT

This invention relates to new compositions of matter for use in treating wrinkling of the human skin. The compositions comprise, as an essential ingredient therein, at least one N-acylate, by butyric acid, of an alpha-amino acid or a salt of said acylate with an inorganic, organic or biologic base or with a metal.

7 Claims, No Drawings

USE OF COMPOSITIONS OF MATTER CONTAINING N-ACYLATES OF ALPHA AMINOACIDS FOR THE TREATMENT OF SKIN

This is a continuation of application Ser. No. 748,777 filed June 25, 1985, now abandoned, which in turn is a continuation of application Ser. No. 567,767 filed Jan. 3, 1984, now abandoned, which in turn is a continuation-in-part of application Ser. No. 358,848 filed Mar. 17, 1982, now abandoned.

The present invention relates to the treatment of skin with compositions of matter wherein the active ingredient is at least one N-acylate of alpha-aminoacid or of a mixture of the same. It is known to acylate aminoacids or mixtures of the same by fatty acids comprising more than five carbon atoms in the chain. However, these known acylates are liposoluble but generally insoluble in water and in usual solvents.

The applicants have discovered that acylation of alpha-aminoacids or of mixtures of the same by butyric acid leads to new acylates which are simultaneously liposoluble and soluble in water and in a large variety of polar and nonpolar solvents. Particularly, the N-acylation of aminoacids or of mixtures of the same by butyric acid gives products soluble in alcohol, ketones ethylacetate, benzene, chloroform, diethyl ether and the like. Of course, the liposolubility, the hydrosolubility and the solubility in various solvents, vary in relationship with the nature of the aminoacids. These acylates are also soluble in mixtures of polar and nonpolar solvents such as methanol and chloroform but are insoluble in petroleum ether, in hexane and, for some of them, in isopropyl ether.

Compared with the lipoaminoacids obtained by acylation of aminoacids or of mixtures of the same of fatty acids comprising more than five carbon atoms of the chain, the acylation by butyric acid leads to compounds presenting a higher acidifying power of strictly biological origin (this is the acidity of the liberated carboxy groups) due to the shorter length of the acylating chain.

The compounds of the invention present a better penetration for instance through the skin and also are efficient at lower doses than the previously known lipoaminoacids.

Accordingly, the present invention relates to new compositions of matter for use in the treatment of skin to alleviate wrinkles, comprising-administering a composition having as an essential ingredient therein at least one N-acylate, by butyric acid, of an alpha-aminoacid or a salt of said acylate with an inorganic, organic or biologic base or with a metal.

According to the invention the alpha-aminoacid may be replaced by a mixture of the same obtained by any appropriate route and for instance the mixture of aminoacids obtained by the complete hydrolysis of a protein.

The result of the acylation by butyric acid of an aminoacid or of a mixture of aminoacid gives, in all cases, N-acylated derivatives; however, for those aminoacids that present other basic functions, these functions may also be partially or completely acylated by butyric acid.

As to the salts in these N-acylates of aminoacids or of mixtures of the same, it is to be understood the salts obtained by the action of any appropriate inorganic or organic bases (for instance triethanolamine, diethylamine and morpholine the various known basic aminoacids such as lysine, arginine, or nithine) or biologic bases like choline, guanidine and the like. The corresponding salts are obtained by mere reaction of the previously obtained N-acylates on the selected base. As to the obtention of metal salts of the N-acylates of the invention they may be easily obtained by reacting the N-acylates on the hydroxide or carbonate of the selected metal in warm conditions; preferred metals are those known as oligo-elements.

For the obtention of the N-acylates of butyric acid according to the present invention, the preferred route comprised the use of butyric anhydride which allows a complete reaction of the aminoacid with concomittent liberation of free butyric acid; an excess of 10-25% with respect to stoichiometric proportions is preferred but when the aminoacid treated comprise other functions that might be acylated, it will be necessary to take into account all these functions in order to determine the appropriate proportions of butyric anhydride to use. The invention will be better understood from the description of the following examples:

EXAMPLE 1—Butyryl glycine

In a 500 ml reactor fitted with stirring means and warmed by a water bath, are poured 30 g (0.4 mol) of glycine, then slowly under stirring, 40 ml of sodium hydroxide solution at 30%. When the reaction mixture is clear, there is slowly added 65 g of butyric anhydride, while maintaining pH between 10 and 10.5 by the end of the addition (temperature 40-45° C.). The reacting mixture is thus warmed at 70° C. for half an hour and allowed to cool. For obtaining butyryglycine from its sodium salt, hydrochloric acid is slowly added under stirring, until pH is reached. This leads to the appearance of an oily supernatant phase which is separated and distillated under reduced pressure (oil-bath) for elimination of water and hydrochloric acid. After cooling, there is added petroleum ether for precipitation of butyrylglycine and elimination of butyric acid; this treatment is repeated twice.

Yield 51 g (88%) of a product, the analysis of which shows a perfect correspondence with the theory. (Mol. Weight 145; $C_6H_{11}NO_3$) Acid index found: 382 (Theory: 386).

EXAMPLE 2 —Butyryl phenylalanine

This preparation is conducted as in example 1 with 33 g (0.2 mol) of phenylalanine and 36 g of butyric anhydride.

Yield 42 g (90%) of a product, the analysis of which shows a perfect correspondence with the theory. (M.W. 235; $C_{13}H_{17}NO_3$) Acid index found: 235 (Theory: 238).

EXAMPLE 3—Butyrylthreonine

This preparation is conducted as in example 1 with 36 g (0.3 mol) of threonine and 51 g of butyric anhydride.

Yield 57 g (99%) of a product, the analysis of which shows a perfect correspondence with the theory. (M.W. 189; $C_{13}H_{15}NO_4$) Acid index found: 293 (Theory: 296).

EXAMPLE 4 —Butyrylaspartic acid

This preparation is conducted as in example 1 with 53 g (0.4 mol) of aspartic acid and 64 g of butyric anhydride; but after the stage of elimination of water and hydrochloric acid, it is necessary to eliminate the remaining butyric acid by distillation under reduced pressure at 130°-140° C. (oil-bath). The anhydrous residue is treated by an equal weight of distillated water, then by carbon black.

Yield 75 g (94%) of a product, the analysis of which shows a perfect correspondence with theory. (M.W. 203; $C_8H_{13}NO_5$) Acid index found: 382 (Theory: 386).

EXAMPLE 5—Butyrylvaline

This preparation is conducted as in example 1, with 58 g (0.5 mol) and 85 g of butyric anhydride. As the butyrylvaline is poorly soluble in cold water, the elimination of butyric acid is made by washing with icy water.

Yield 85 g (92%) of a product, the analysis of which shows a perfect correspondence with the theory (M.W. 187; $C_9H_{17}NO_3$) Acid index found: 294 (Theory: 297).

EXAMPLE 6—Butyryl leucine

This preparation is conducted as in example 1, with 65 g of leucine (0.5 mol) and 85 g of butyric anhydride; the elimination of butyric acid is effected as in example 5 for butyrylleucine is poorly soluble in cold water.

Yield 89 g (92%) of a product, the analysis of which shows a perfect correspondence with the theory (M.W. 201; $C_{10}H_{19}NO_3$) Acid index found: 277 (Theory: 280).

EXAMPLE 7—Dibutyryl lysine

This preparation is conducted as in example 1 with 60 g of a 50% solution of lysine (0.2 mol) and 64 g of butyric anhydride for the dibutyric derivative.

Yield 51 g (85%) of a product, the analysis of which shows a perfect correspondence with the theory (M.W. 286; $C_{14}H_{26}N_2O_2$) Acid index found: 193 (Theory: 195).

EXAMPLE 8—Butyrylproline

This preparation is conducted as in example 1 with 23 g (0.2 mol) of proline and 40 g of butyric anhydride.

Yield 34 g (92%) of a product, the analysis of which shows a perfect correspondence with the theory (M.W. 185; $C_9H_{15}NO_3$) Acid index found: 304 (Theory: 302).

EXAMPLE 9—Mono and dibutyryl hydroxyproline

This preparation is conducted as in example 1 with 52 g (0.4 mol) and 75 g of butyric anhydride.

Yield 75 g (87%) of a product, the analysis of which shows a mixture at the mono- (35%) and di-substituted (65%) forms, for which the theory is: M.W. 201, $C_9H_{15}NO_4$, acid index 279 for monoM.W. 271, $C_{13}H_{21}NO_5$, acid index 207 for diFound value for acid index is 230.

EXAMPLE 10—Dibutyrylhydroxylysine

This preparation is conducted as in example 1, with 32 g (0.2 mol) of hydroxylysine and 40 g of butyric anhydride.

Yield 53 g (88%) of a product, the analysis of which shows a perfect correspondence with the theory (M.W. 302; $C_{14}H_{26}N_2O_5$) Acid index found: 187 (Theory: 184).

EXAMPLE 11—Butyryl methionine

This preparation is conducted as in example 1 with 45 g (0.3 mol) of methionine and 50 g of butyric anhydride.

Yield 61 g (92%) of a product, the analysis of which shows a perfect correspondence with the theory (M.W. 219; $C_9H_{17}NO_3S$) Acid index found: 257 (Theory: 255).

EXAMPLE 12—Dibutyryl Cystine

This preparation is conducted as in example 1 with 48 g (0.2 mol) of cystine and 64 g of butyric anhydride.

Yield 73 g (91%) of a product, the analysis of which shows a perfect correspondence with the theory (M.W. 380; $C_{14}H_{24}N_2O_6S_2$) Acid index found: 305 (Theory: 294).

EXAMPLE 13—Butyrylcysteine

This preparation is conducted as in example 1 with 48 g (0.4 mol) of cysteine and 64 g of butyric anhydride.

Yield 71 g (97%) of a product, the analysis of which shows a perfect correspondence with the theory (M.W. 191; $C_7H_{13}NO_3S$) Acid index found: 307 (Theory: 297) SH found: 16.8 (Theory: 17.1).

The following examples relate to the preparation of acylates by butyric acid of non separated mixtures of aminoacids obtained by the complete hydrolysis of natural proteins. As these mixtures retain substantially the quantitative and qualitative proportions of aminoacids existing in the starting proteins, they are identified by a similar name.

The first step comprises the preparation of the protein hydrolysat from the selected protein. 200 g of the protein are treated conventionally by concentrated hydrochloric acid and the absence of peptides is checked by the Biuret test, after what the solution is neutralized (pH 6.5-7) treated by carbon black and filtered. The solution thus obtanned is titrated by formaldehyde, for the determination of amine functions available for acylation and of the amount of butyric anhydride to be used. With a sample of the hydrolysate a dry extract is prepared, weighed, treated by methanol for the elimination of sodium chloride and once more titrated by formaldehyde.

This preliminary work allows to start the acylation with the appropriate proportions of reactants.

EXAMPLE 14—Butyrylcollagenic acid

The starting protein is gelatin. The average molecular weight of the aminoacids of the hydrolysate is 110. 200 ml of the titrated hydrolysate, containing about 50 g of aminoacids are treated as described in example 1, by 80 g of butyric anhydride. The separation of the acylate is conducted by distillation as in example 4 above and leads to 74 g (92%) of a product, the analysis of which shows a good correspondence with the theory. Nitrogen titration found: 8.2% (Theory: 8%) Acid index found: 335 (Theory: 327).

EXAMPLE 15—Butyrylkeratinic acid

The starting protein is horn. The average molecular weight of the aminoacids of the hydrolysate is 120. The dosage of acylable amine functions is made with reference to cystine. The preparation is conducted as in example 14 above from 300 ml of hydrolysate and 80 g of butyric anhydride; for obtaining a better solubility of the acylates of valine, leucine and isoleucine, 3 to 5% of propyleneglycol are added.

Yield 87 g (96%) of a product, the analysis of which shows an acceptable correspondence with the theory. Nitrogen titration found: 8.2% (Theory 7.4%); the difference comes from the presence of dibasic compounds in the mixture. Acid index found: 287; for the butyryl cystine, the theory is 294.

EXAMPLE 16—Butyrylcaseinic acid

The starting protein is casein. The average molecular weight of the aminoacids of the hydrolysate is 120. The preparation is conducted as in example 14 above, from 300 ml of hydrolysate containing about 41 g of aminoacids and 60 g of butyric anhydride.

Yield 63 g (95%) of a product, the analysis of which shows a good correspondence with the theory. Nitrogen titration found: 8.2% (Theory 7.3%). Acid index found: 260 (Theory 253).

The compositions according to the invention comprise a pharmaceutically acceptable carrier together with an amount of the active ingredient effective to achieve an anti-wrinkle effect. This amount will generally be from 0.1 to 10% in weight of active ingredient together with an appropriate carrier; the use of higher contents of active substances is generally not necessary. Examples of various compositions are given below.

The method of the present invention was compared to known methods utilizing the administration of palmitoylhydroxyproline as the active ingredient. These methods have been known for about three years and consist of twice daily topical application of a composition containing 3% by weight palmitoylhydroxyproline as the active ingredient. In tests on approximately 100 cases, the butyryl derivatives were found to be far more effective. Butyryl hydroxyproline administered one every two days at an active ingredient level of only 1% by weight showed improvement as great as that with the palmitoylhydroxyproline administered twice daily at the 3% level. In each case at least 25% of the treated individuals showed a clearly improved state after one week as compared to controls treated with only the inert carrier.

It will be understood that it is intended to cover all changes and modifications of the preferred embodiment of the invention herein chosen for the purpose of illustration which do not constitute a departure from the spirit and scope of the invention.

What is claimed is:

1. A method of treating wrinkles of the human skin, said method comprising the topical administration of a composition comprising as an active ingredient at least one N-acylate selected from the group consisting of butyrylglycine, butyryl phenylalanine, butyrylthreonine, butyrylaspartic acid, butyrylvaline, butyryl leucine, dibutyryl lysine, butyrylproline, mono and dibutyryl hydroxyproline, dibutyrylhydroxylysine, butyryl methionine, dibutyryl cystine, butyrylcysteine, butyrylcollagenic acid, butyrylkeratinic acid and butyrylcaseinic acid, said composition comprising a pharmaceutically acceptable carrier and an amount of said active ingredient effective to treat wrinkles.

2. The method of claim 1 wherein said active ingredient is present in an amount from 0.1% to 10% by weight.

3. A method of treating wrinkles of the human skin, said method comprising the topical administration of a composition comprising as an active ingredient at least one N-acylate, said N-acylate being formed by butyric acid acylation of at least one alpha-aminoacid or a salt of said N-acylate, said composition comprising a pharmaceutically acceptable carrier and an amount of said active ingredient effective to treat wrinkles.

4. The method of claim 3 wherein said active ingredient is present in an amount from 0.1% to 10% by weight.

5. The method of claim 3 wherein said active ingredient in said composition is butyrylhydroxyproline.

6. The method of claim 5 wherein the active ingredient is present in the amount of about 1% by weight of the composition and the composition is topically administered to the area to be treated once every two days.

7. A method of treating wrinkles of the human skin, said method comprising the topical administration of a composition comprising as an active ingredient at least one N-acylate being the result of the butyric acid acylation of a mixture of alpha-aminoacids obtained by the complete hydrolysis of one or more proteins, said composition comprising a pharmaceutically acceptable carrier and an amount of said active ingredient effective to treat wrinkles.

* * * * *